United States Patent [19]

Granelli et al.

[11] Patent Number: 5,359,140

[45] Date of Patent: Oct. 25, 1994

[54] UREA PRODUCTION PROCESS OF HIGH ENERGY EFFICIENCY

[75] Inventors: Franco Granelli, Milan; Giuseppe Carloni, San Donato Milanese, both of Italy

[73] Assignee: Snamprogetti S.p.A., Milan, Italy

[21] Appl. No.: 854,298

[22] Filed: Mar. 19, 1992

[30] Foreign Application Priority Data

Mar. 22, 1991 [IT] Italy ............... MI91-A-000778

[51] Int. Cl.⁵ ............................ C07C 273/04
[52] U.S. Cl. ............................ 564/67; 564/66; 564/69; 564/70; 564/71; 564/72
[58] Field of Search ............... 564/67, 69, 70, 71, 564/72, 66

[56] References Cited

U.S. PATENT DOCUMENTS 4,208,347 1/1980 Pagani .................. 564/70

FOREIGN PATENT DOCUMENTS

| | | |
|---|---|---|
| 0098396 | 1/1984 | European Pat. Off. |
| 0213669 | 3/1987 | European Pat. Off. |
| 417830A | 3/1991 | European Pat. Off. |
| 2087381A | 5/1982 | United Kingdom. |

*Primary Examiner*—Shailendra Kumar
*Attorney, Agent, or Firm*—Rogers & Wells

[57] ABSTRACT

A urea production process in which the urea solution produced in the reaction zone is treated in sequence with a first thermal decomposer at the same pressure as the reaction, to decompose part of the residual ammonium carbamate into its components, then with an adiabatic stripper in which the free ammonia is stripped with $CO_2$ operating at a pressure which is 1-7 MPa less than the synthesis pressure, then with two further carbamate thermal decomposition stages at decreasing pressures. The gaseous products obtained from those stages at pressures less than the synthesis pressure are mixed with the recycle solutions from the downstream stages, condensed by heat transfer against said downstream stages, and then recycled to the reaction as liquid.

12 Claims, 1 Drawing Sheet

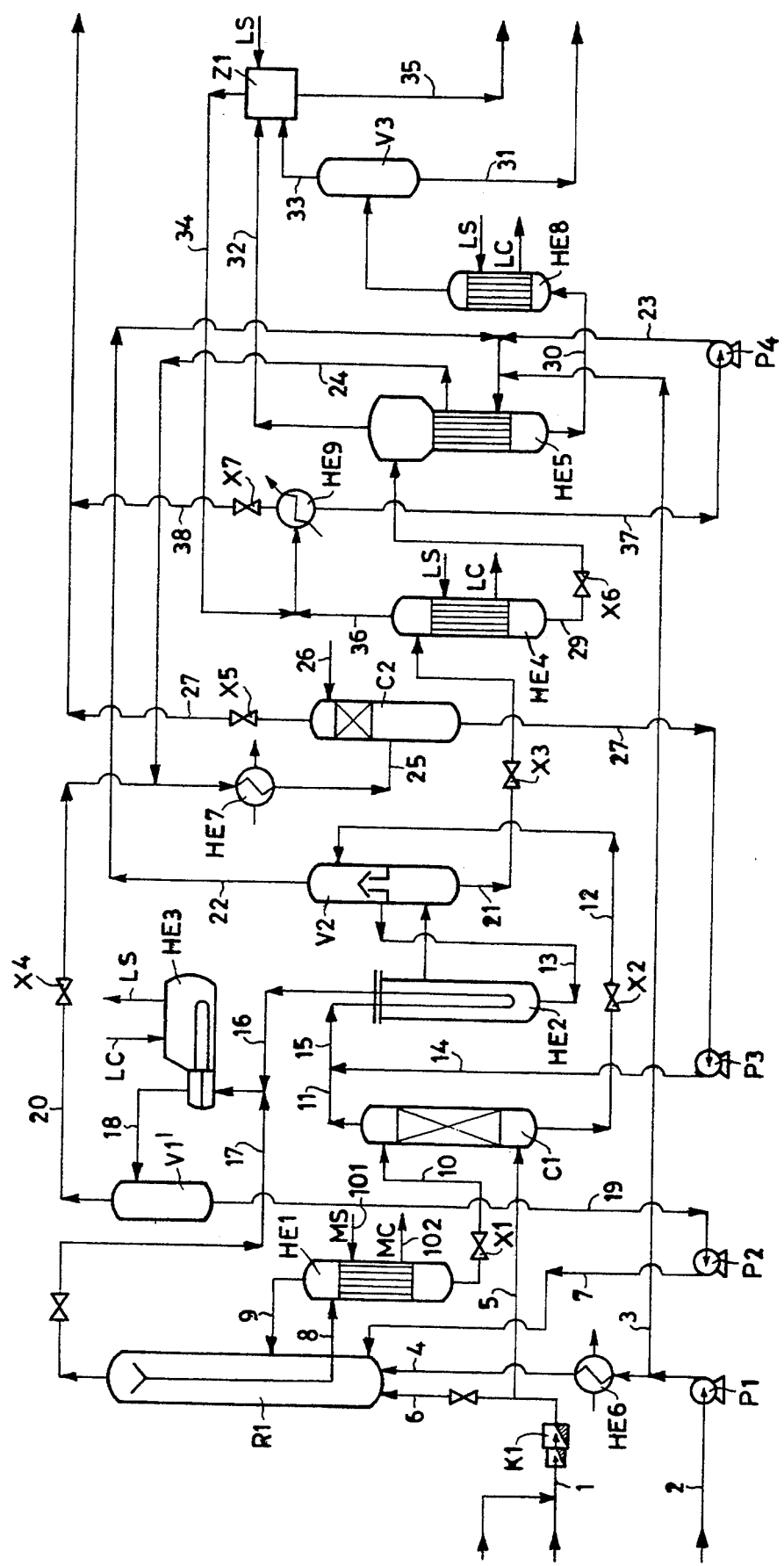

UREA PRODUCTION PROCESS OF HIGH ENERGY EFFICIENCY

BACKGROUND OF THE INVENTION

This invention relates to urea production and in particular to a urea synthesis process of high energy efficiency starting from ammonia and carbon dioxide.

In the known art, industrial urea production processes are based on the synthesis of ammonium carbamate at high temperature (for example 175°–250° C.) and pressure (for example 12–25 MPa) from ammonia and carbon dioxide in accordance with the exothermic reaction:

$$2NH_3 + CO_2 \rightleftharpoons NH_2COONH_4$$

which is then dehydrated to urea in the same reaction zone and under the same conditions in accordance with the endothermic reaction:

$$NH_2COONH_4 \rightleftharpoons NH_2CONH_2 + H_2O$$

which proceeds consecutively with the ammonium carbamate formation.

Whereas under the stated conditions the first reaction is very fast and is strongly shifted towards the right, the carbamate dehydration reaction is slower and only partly shifted towards the right. The degree of conversion of carbamate to urea depends on the stated operating conditions, on the residence time in the reactor and on the excess of ammonia over the stoichiometric ratio between the ammonia and the carbon dioxide.

To obtain high conversion to urea and limit the formation of harmful by-products such as biuret and its homologues, the $NH_3/CO_2$ molar ratio maintained in the reaction zone in industrial processes varies between 2.5 and 5.

The effluent obtained from the synthesis zone consists substantially of a solution of urea, water, unconverted ammonium carbamate and free ammonia.

The free ammonia and the ammonium carbamate contained in said effluent must be separated and recycled to the synthesis section for total conversion to urea, so that substantially only the product urea and its stoichiometric water are discharged from the plant, in accordance with the overall equation:

$$2NH_3 + CO_2 \rightleftharpoons NH_2CONH_2 + H_2O$$

according to which each mole of urea produced is accompanied by one mole of water, generated by the dehydration of the carbamate. In certain industrially successful processes, such as those of GB patent 2087381 in the name of Snamprogetti and U.S. Pat. No. 4,208,347 in the name of Montedison, an initial recovery of the unconverted carbamate is effected in a first decomposer operating under the same pressure as the synthesis reactor, to thermally decompose part of the unconverted ammonium carbamate to urea and release a part of the dissolved free ammonia, by heating the solution by heat transfer with a heating fluid, normally medium pressure steam, preferably in vertical heat exchangers in which the urea solution flows as a thin film to facilitate mass transfer between the phases.

The ammonium carbamate decomposition can optionally be facilitated by a gaseous ammonia stream fed into the bottom of the first decomposer. Alternatively, the ammonia contained in excess in the effluent can be used as a self-stripping agent.

In those processes comprising a first decomposition stage at the same pressure as the synthesis reaction, the vapour produced by the carbamate decomposition is generally recycled to the synthesis zone. This recycling can be conducted either directly in the gaseous phase to thermally sustain the reactor, or by separately recovering part of the heat of condensation of the gaseous phase produced in the decomposer to produce steam for use in other plant sections, and feeding the recycle stream as a mixed phase to the reactor.

A urea solution containing a reduced quantity of carbamate and an excess of free ammonia is obtained from this first decomposition stage.

It has been proposed, for example in European Patent 98396 in the name of Montedison, to follow the first carbamate decomposition stage with an excess ammonia removal stage, conducted at the same pressure as the synthesis zone, comprising stripping in countercurrent with a stream of carbon dioxide in a film heat exchanger, but with the simultaneous supply of heat on the shell side by condensing steam limited to the upper part of the tube bundle. The lower part of the tube bundle therefore operates under adiabatic conditions. From the description of this patent it emerges however that this adiabatic part of the residual free ammonia removal process results in a high residual carbamate content in the urea solution, hence highly penalizing the subsequent plant sections which then have to recover the carbamate under energy-unfavourable conditions, so considerably increasing energy consumption.

European patent 213669 in the name of Stamicarbon proposes adiabatically stripping the urea solution leaving the reaction zone with part of the feed carbon dioxide at the reaction pressure, but without preceding it by a first thermal decomposition stage. This treatment is limited only to a minor portion of the effluent (30–50%) whereas the major portion (50–70%) is fed to conventional stripping with carbon dioxide using an external heat supply.

In this process only the minor portion is fed to the subsequent medium pressure carbamate decomposition stage, its heat of condensation being recovered at a convenient temperature level only for this minor part, whereas the major part is directly fed to the low pressure thermal decomposition stage, where the heat of condensation of this major part is recovered at a temperature too low for its convenient use in the plant, and has to be disposed of with the cooling water, so energy-penalizing the overall process. This process is also difficult to implement in terms of correctly maintaining the division of the parallel streams which follow these separate paths.

SUMMARY OF THE INVENTION

The present invention provides a urea synthesis process which overcomes the drawbacks of the aforementioned processes by comprising a cycle of high energy efficiency.

According to the invention the urea solution leaving the first thermal decomposer at the same pressure as the synthesis is treated in an adiabatic stripping zone with carbon dioxide at a pressure 1–7 MPa lower than the synthesis pressure, to obtain from the top a vapour mixture consisting substantially of ammonia, carbon dioxide and water.

According to the invention, this gaseous stream is mixed with the liquid recycle stream from the medium pressure carbamate recovery stage and then condensed by heat transfer to the urea solution subjected to carbamate recovery at medium pressure (1–4 MPa). According to the invention, the vapour mixture obtained from this medium pressure recovery stage is mixed with the recycle solution at low pressure (about 0.35 MPa) and then condensed at a temperature level which enables its heat to be effectively used in the final vacuum concentration stages of the urea solution. In this respect, the resultant mixture has an $NH_3/CO_2$ ratio around the "azeotropic" point, ie the point in which the compositions of the liquid phase and vapour phase coincide to provide condensation at the highest possible temperature, which in the process according to the invention allows useful recovery of the latent heat even of the gaseous phase produced in the medium pressure stage.

This manner of operating results in very efficient recovery of the heat of condensation of the carbamate, significantly improving the energy efficiency of the process. The method of condensing the decomposition product at medium pressure with an $NH_3/CO_2$ molar ratio around the azeotropic point enables the added dilution water from this condensation to be reduced to a minimum, so minimizing the recycling of water to the synthesis zone and hence significantly improving the conversion of ammonium carbamate to urea, which is hindered by the presence of water.

DESCRIPTION OF THE PREFERRED EMBODIMENTS

The process according to the invention consequently comprises the following treatment stages:

the high pressure reaction zone operates with a $NH_3/CO_2$ molar ratio of between 2.5 and 5, and preferably between 3.5 and 4.5, at a temperature of 175°–220° C. and preferably 185°–200° C., and at a corresponding pressure of 13–23 MPa, to produce a urea solution containing unconverted ammonium carbamate and free ammonia. The reaction conditions are chosen such as to obtain conditions of substantial equilibrium between liquid and vapour in the reactor, the reaction mixture being practically under boiling, taking account of the presence of uncondensables;

the solution obtained from the reaction zone is fed to a first decomposer operating at 200°–210° C., in which a first part of the ammonium carbamate decomposes under addition of heat and a part of the ammonia dissolved in the effluent from the reactor is released, operating substantially at the same pressure as the reaction zone and recycling as gas to the reaction zone the gaseous products of this first decomposer;

the urea solution produced by the first decomposer, and having a ratio of the $NH_3$ to the $CO_2$ unconverted to urea of between 6 and 12 and preferably between 8 and 10, is fed to an adiabatic stripper in which the free dissolved ammonia is stripped from the solution by countercurrent contact with a prevailing part, of more than 70% and preferably more than 90%, or with all the carbon dioxide fed to the plant, operating at a pressure which is 1–7 MPa lower, and preferably 2–5 MPa lower, than the pressure of the reaction zone;

the urea solution obtained from the adiabatic stripper has a molar ratio of the $NH_3$ to the $CO_2$ unconverted to urea of between 2.0 and 4.0 and preferably between 2.5 and 3.5. It is fed to a second thermal decomposition zone at medium pressure of between 1 and 4 MPa, in which the heat required for the decomposition is provided by condensing the vapour mixture obtained from the preceding adiabatic stripping stage after being mixed with the recycle carbamate solution from the medium pressure decomposition stage;

the liquid-vapour mixture from the partial condensation of the vapour produced in the adiabatic stripper, used for thermally sustaining the second decomposer, is fed to a second final condensation zone, in which steam is produced usable in other plant sections, and is then recycled in the liquid phase to the synthesis reactor;

the vapour mixture obtained from the second decomposer operating at medium pressure is condensed with an ammonia/carbon dioxide molar ratio in the condensate of between 2 and 4, and preferably between 2.5 and 3.5, in at least one condensation stage operating at the same pressure as the second decomposer. The heat of condensation is used to concentrate the urea solution in the next concentration zone. The resultant condensate is that which is recycled to the first condensation zone and mixed with the vapour from the stripping with $CO_2$ before their condensation for thermally sustaining the second decomposer;

the urea solution produced in the second decomposer is fed into at least one further ammonium carbamate thermal decomposition zone before being fed to the concentration section to produce a concentrated urea solution for subjecting to final prilling or granulation treatment.

The disclosed process provides to insert a further stage of adiabatic stripping with $CO_2$, at a pressure which is lower than the synthesis pressure (1–7 MPa less), to the traditional scheme of the urea production process—as for example the process according to the copending European application N.417830 A of the same applicant—which is characterized by associating to the stage of synthesis, a stage of stripping at the same pressure as the synthesis reaction and two following stages of decomposition and recovery of the residual carbamate at medium pressure (1–3 MPa) and at low pressure (0.3–0.5 MPa).

This additional stage deeply modifies the process stages and its economy.

With reference to the process scheme disclosed in EP 417830, the following significant differences can be observed.

The present invention provides to use all or the most part of the carbon dioxide (at least the 70% of the fed and preferably the 90% and more) for the adiabatic stripping of the residual carbamate in the additional stage (column C1 of the present application) at a still high pressure, which enables to recover its condensation heat at a good temperature and with a low energy of recycle. This stage allows to remove a substantial part of the reagents unconverted to urea from the reaction product still at high pressure, near to the reaction pressure, considerably reducing the work of the recovery and recycle sections of such components in the following lower pressure stages.

The gaseous stream generated by this new stage, is used similarly to the products of the self-stripping stage occurring at the same pressure as the synthesis reaction according to the previous application.

According to the previous application a little part of $CO_2$, no more than 20%, is used in the non-adiabatic stripping, but using also the heat coming from the heat-exchanger HE2 (column C1 of the cited application) at a pressure of 1–3 MPa. In the previous application, the gaseous product of the stripping stage occurring at the same pressure as the synthesis reaction, is fed to the condensation and the heat recovery system of the exchangers HE2–HE3, in order to produce a low value vapour mixture at low pressure. In the present application such heat is directly used to sustain the synthesis reaction, namely at the highest temperature, and then the gaseous mixture can be fed together with the larger part of the carbamate which has been preformed downstream.

In the present application, the zone Z1 of recovery and separate recycle of the ammonia, present in the previous application, has been eliminated.

The characteristics and advantages of the process according to the invention will be more apparent from the description of a typical embodiment thereof given hereinafter and illustrated by way of example on the schematic flow diagram of the Figure.

BRIEF DESCRIPTION OF THE DRAWING

The plant shown on the flow diagram of the FIGURE is for a daily production of 360 tonnes of urea, equivalent to an hourly capacity of 15000 kg/h.

EXAMPLE

The plant is fed through the line 1 with 11000 kg/h of $CO_2$ and 100 kg/h of inerts and air as passivation agent. This feed is compressed to a pressure of 16 MPa by the compressor K1 and is fed through the line 5 to the adiabatic stripping column C1. The line 6 which feeds the $CO_2$ to the reactor is kept closed.

8500 kg/h of $NH_3$ are fed to the plant through the line 2 at a temperature of 30° C. and are pumped to a pressure of 19 MPa by the pump P1. 850 kg/h of ammonia are fed from its delivery side to the medium pressure condensation zone through the line 3, while the remaining 7650 kg/h are fed directly to the synthesis reactor R1 through the line 4 after being heated in the preheater HE6 to 140° C.

A recycle carbamate stream consisting of 13759 kg/h of $NH_3$, 14422 kg/h of $CO_2$ and 4561 kg/h of water is fed through the line 7 to the reactor R1.

The volume of the reactor R1 is such as to provide a residence time of 35 minutes for the reaction mixture. The ammonium carbamate is dehydrated to urea in the reactor, a urea solution consisting of 16865 kg/h of $NH_3$, 4787 kg/h of $CO_2$, 9594 kg/h of water and 15600 kg/h of urea being extracted from its top at a pressure of 18.5 MPa and temperature of 190° C., and fed to the falling film decomposer HE1.

In the decomposer HE1 the urea solution is heated to a temperature of 209° C. using the heat of condensation of 6450 kg/h of saturated steam at 2.2 MPa fed to the shell side of the heat exchanger HE1 through the line 101. The condensate is extracted through the line 102.

From the top of the first decomposer HE1 a gaseous stream is obtained consisting of 4396 kg/h of ammonia, 1815 kg/h of carbon dioxide and 368 kg/h of water, and is recycled through the line 9 to the reactor R1. A urea solution at 209° C. and 18.5 MPa is obtained from the bottom of HE1, consisting of 12809 kg/h of ammonia, 3412 kg/h of carbon dioxide, 9046 kg/h of water and 15000 kg/h of urea, with a molar ratio of $NH_3$ to $CO_2$ unconverted to urea of 9.7.

This stream is expanded through the valve X1 to a pressure of 16 MPa, with a pressure drop of 2.5 MPa, and is fed through the line 10 to the top of the stripping column C1. In this column, which is packed, a considerable part of the free ammonia present in the urea solution is stripped off by the effect of the stripping $CO_2$ which rises through the column in countercurrent after being fed through the line 5.

From the top of C1 a vapour mixture is obtained composed of 7565 kg/h of $NH_3$, 8624 kg/h of $CO_2$, 886 kg/h of water and 100 kg/h of inerts at a temperature of 203° C., and is fed through the line 11 to the condensation zone. From the bottom of C1 a urea solution is obtained at a temperature of 165° C. comprising 5244 kg/h of $NH_3$, 5788 kg/h of $CO_2$, 8160 kg/h of water and 15000 kg/h of urea, and is expanded to 1.8 MPa through the valve X2 and fed through the line 12 to the separator V2 which is provided with a chimney plate.

After the flash vapour has been separated the urea solution is circulated via the line 13 through the shell side of the heat exchanger HE2, which receives via the line 11 the vapour produced in the column C1, and via the line 14 the recycle carbamate solution from the medium pressure condensation zone at a temperature of 97° C. and consisting of 6419 kg/h of $NH_3$, 6175 kg/h of $CO_2$ and 3763 kg/h of water.

The resultant liquid-vapour mixture has a temperature of 172° C. and enters the heat exchanger HE2 through the line 15, to leave it through the line 16 at a temperature of 165° C. and with a liquid molar fraction of 84%, after transferring part of its heat of condensation to the urea solution occupying the shell side of the heat exchanger.

The final condensation of this stream is achieved in the heat exchanger HE3, in which the liquid-vapour mixture from the line 16 and the vapour extracted from the top of the reactor R1 at a temperature of 190° C. and comprising 100 kg/h of $NH_3$, 10 kg/h of $CO_2$ and 15 kg/h of water are condensed at a temperature of 155° C. and the resultant heat of condensation is used to produce 4950 kg/h of saturated steam at 4 bar (0.4 MPa) and 151° C.

The condensed mixture leaving the heat exchanger HE3 is fed via the line 18 to the separator V1, where the separated liquid phase comprises 13759 kg/h of $NH_3$, 14422 kg/h of $CO_2$ and 4561 kg/h of water, and is recycled to the reactor via the line 19, the pump P2 and the line 7. The gaseous phase consists of 325 kg/h of $NH_3$, 387 kg/h of $CO_2$, 103 kg/h of water and 100 kg/h of inerts and is fed to the medium pressure recovery section via the line 20 and the control valve X4.

A urea solution is obtained from the bottom of the separator V2 at a temperature of 160° C. consisting of 1180 kg/h of $NH_3$, 481 kg/h of $CO_2$, 15000 kg/h of urea and 5985 kg/h of water, and is fed through the line 21 to the next thermal decomposition section, after expansion to a pressure of 0.35 MPa through the valve X3. The vapour obtained from the top of the separator/consists of 4064 kg/h of $NH_3$, 5037 kg/h of $CO_2$ and 2175 kg/h of water at a temperature of 140° C., and is fed through the line 22 to the heat exchanger HE5. Before entering said heat exchanger, this stream is mixed with the recycle ammonium carbamate solution fed through the line 23 and consisting of 1180 kg/h of $NH_3$, 481 kg/h of $CO_2$ and 1385 kg/h of water, and with 850 kg/h of $NH_3$ fed through the line 3. In this respect, it has been surprisingly found that this addition of ammonia, which would appear damaging to the useful temperature level for heat recovery in HE5, results in an overall improvement in the recycling, and easier removal in C2 of the products to be recycled upstream, by releasing the uncondensables to be discharged from the cycle.

The vapour is partly condensed in the heat exchanger HE5 and its heat of condensation is used for the vacuum concentration of the urea solution from the low pressure decomposition stage. The liquid-vapour mixture leaving this heat exchanger at a temperature of 110° C. is fed through the line 24 to the heat exchanger HE7 together with the mixture of vapour and uncondensables from V1. Virtually total vapour condensation takes place in the heat exchanger HE7 with the exception of the inerts. The condensation product at a temperature of 97° C. is fed via the line 25 to the wash column C2, where the inerts (100 kg/h) are released and washed before being discharged to atmosphere via the valve X5 and the line 28. Washing is conducted with 100 kg/h of water fed through the line 26.

The ammonium carbamate solution obtained from the bottom of the column at a temperature of 97° C. consists of 6419 kg/h of $NH_3$, 6175 kg/h of $CO_2$ and 3763 kg/h of water, and is recycled via the line 27 and pump P3 to the high pressure condensation section in HE2. The urea solution leaving the separator V2 is fed to the falling film heat exchanger HE4 in which operating at a pressure of 3.5 bar (0.35 MPa) a further part of the ammonium carbamate is decomposed to obtain from the bottom a urea solution at a temperature of 138° C., composed of 375 kg/h of $NH_3$, 125 kg/h of $CO_2$, 15000 kg/h of urea and 5333 kg/h of water. The heat of decomposition is provided by the condensation of 1200 kg/h of steam at 3.5 bar fed to the shell side of the heat exchanger. The urea solution is fed via the line 29 and control valve X6 to the two-stage concentration section.

The operating pressure in the first falling film concentrator HE5 is 0.35 bar abs. (35 KPa absolute), using as the heat source the heat of condensation of the gaseous phase produced in the medium pressure decomposer, to obtain a concentrated urea solution of 94% by weight. This concentrate is fed through the line 30 to the final concentration stage comprising the heat exchanger HE8, fed with 1450 kg/h of low pressure steam, and the separator V3, from which a urea melt comprising 15000 kg/h of urea and 30 kg/h of water is obtained.

The vapours produced in the concentration stages HE5 and HES/V3 are fed via the lines 32 and 33 to the condensation and effluent treatment zone Z1, to which 2300 kg/h of low pressure steam are fed, for vacuum vapour extraction and for stripping the ammonia and carbon dioxide contained in the process condensate.

The following streams are obtained separately from the section Z1:

a gaseous stream containing 375 kg/h of ammonia, 125 kg/h of carbon dioxide and 733 kg/h of water, which is recycled via the line 34 to the low pressure condensation section;

a liquid stream consisting of 6870 kg/h of purified water at 139° C., which is discharged from the plant via the line 35 after recovering its sensible heat by preheating the reactor ammonia feed in the heat exchanger HE6.

The recycle vapour from the zone Z1, recycled through the line 34, is mixed with the top vapour stream of the heat exchanger HE4 flowing in the line 36, and then fed to the condenser HE9 to obtain an ammonium carbonate solution at a temperature of 45° C., which is recycled to the medium pressure condensation section in HE5 via the line 37 and pump P4. Any inerts present are discharged via the control valve X7 and the line 38.

The low pressure steam consumption of the plant is satisfied by the steam produced in the condenser HE3.

From this example it is apparent that the process of the invention has low energy consumption, with the following specific utilities consumptions per tonne of product urea, including the utilities required for effluent treatment:

| medium pressure steam: | 430 kg |
| electricity: (excluding $CO_2$ compression) | 20 kWh |
| cooling water: 60 (temperature difference 10° C.) | $m^3$ |

With respect to the cited application EP 417830 of the same applicant, the reduction of the steam use from a value of 470 kg to a value of 430 kg per t of urea, is significative.

It should be considered that an hypotetic plant having a yield to urea of 100% in the reactor (without any recycle), would give a solution wherein 1000 kg of urea together with 300 kg of stoichiometric water are present and which requires 350 kg of steam to be concentrated to 99.8%.

In the process according to the present invention the heat recovery improvement is obtained improving the condensation of the vapour mixture which is produced in the medium pressure decomposition stage.

Such improvement is due to the gaseous mixture composition, which allows the condensation at a thermic value such as to enable an useful heat riutilization in the same plant.

Such vapour mixture ($NH_3 + CO_2 + H_2O$) has an $NH_3/CO_2$ ratio around the "azeotropic" point, ie its condensation occurrs at the highest possible temperature, compatibly with the working pressure and the minimum quantity of dilution water.

Such minimum quantity of water gives a second energetic advantage because the lowest is the water recycled to the reactor, the highest is the conversion yield to urea and consequently the lowest is the reagents quantity unconverted to urea and the necessary heat quantity to recycle them.

In order to recover the heat at the maximum value of temperature during the condensation of the vapour mixture, the best composition of such mixture, coming from the medium pressure decomposition stage, is obtained adding, upstream of such stage, an adiabatic stripper which works at a pressure of 1-7 MPa (and preferably between 2 and 5 MPa) with respect to the synthesis pressure.

In said stripper, a big part of the fresh $CO_2$ is fed, the ammonia in the urea solution is decreased, so that in the downstream stage of medium pressure decomposition, the obtained vapour mixture has an $NH_3/CO_2$ ratio much more suitable than that of the cited application and said mixture is condensed at a higher temperature with a minimum quantity of dilution water.

A further advantage is the plant's simplification. The vapour mixture of the medium pressure decomposition stage, having said $NH_3/CO_2$ ratio suitable for its condensation, is totally condensed, a part in the recovery-condenser HE5 and a part in the condenser HE7. Said mixture is then washed in order to send to the atmosphere, the inerts ($H_2$, CO, $CH_4$, $O_2$, $N_2$ ...) pratically free of $NH_3$. On the contrary it is not necessary to separate $NH_3$ from the solutions obtained in said condensations and then it is not necessary its separate recycle at medium pressure, as in the cited prior art.

The same expedient, namely to adjust the $NH_3/CO_2$ ratio during the condensation, is obtained sending through the line 3, a little part of the fresh ammonia directly to the condenser/recycler HE5 in order to increase the heat recovery and namely its thermic level of condensation. In the plant every heat recovery corresponds to a lower quantity of heat lost in the cooling water, and then to an energetic improvement of the process.

We claim:

1. A process for producing urea comprising:
   (a) reacting ammonia and carbon dioxide in a reactor operating at a temperature of 175°–220° C. and a pressure of 13–23 MPa using an ammonia to carbon dioxide molar ratio of between 2.5 and 5 to produce a urea solution including ammonium carbamate and free ammonia;
   (b) transferring said urea solution to a first decomposer;
   (c) heating said urea solution in said first decomposer to strip part of the free ammonia and decompose a portion of the ammonium carbamate into carbon dioxide and ammonia, said first decomposer being operated at about 200°–210° C. and substantially at the same pressure as the reactor;
   (d) recycling the gaseous carbon dioxide and ammonia from said first decomposer to said reactor for further reaction;
   (e) feeding the urea solution from the first decomposer, wherein the urea solution has a molar ratio of ammonia to carbon dioxide between about 6 and 12, to an adiabatic stripping column and contacting said urea solution in said stripping column with a countercurrent flow of more than 70% of the total carbon dioxide used in the process to remove ammonia and thereby concentrate the urea solution and to form a vapor phase, the stripping column being operated at a pressure which is at about 1–7 MPa less than the reactor pressure;
   (f) feeding the urea solution obtained from said adiabatic stripping column, which solution has a molar ratio of ammonia to carbon dioxide of between about 2.0 and 4.0, to a second thermal decomposition stage operating at a pressure of about 1–4 MPa, and heating said urea solution in said second thermal decomposition stage to form a vapor phase and a further concentrated urea solution;
   (g) feeding said vapor phase from said second thermal decomposition stage to a shell side of a vacuum concentrator to condense said vapor and form a recyclable carbamate solution and using the heat of condensation of said vapor phase to further concentrate the urea solution in said vacuum concentrator;
   (h) mixing said recyclable carbamate solution from said vacuum concentrator with vapor phase from said adiabatic stripping column and partially condensing said resultant mixture to provide heat required for the second decomposition; and
   (i) further condensing said mixture to produce steam and to form a recyclable stream that is returned to the reactor for reaction.

2. A urea production process as claimed in claim 1, comprising the further steps of feeding the concentrated urea solution obtained in step (f) to a third decomposition stage to further concentrate the urea solution and form a vapor phase, condensing the vapor phase to form a recycle solution, and mixing said recycle solution with said vapor phase in step (g) before feeding said vapor phase to the shell side of the vacuum concentrator.

3. A urea production process as claimed in claim 2, wherein fresh ammonia is combined with the vapor phase/recycle solution mixture before feeding the mixture to the shell side of the vacuum concentrator.

4. A urea production process as claimed in claim 3, wherein the mixture is condensed in said vacuum concentrator at an $NH_3/CO_2$ molar ratio of between about 2.5 and 3.5 and the heat of condensation is used to concentrate the urea solution at a pressure of between 30 and 100 KPa absolute.

5. A urea production process as claimed in claim 4, wherein the mixture is condensed with an $NH_3/CO_2$ ratio close to the azeotropic point of the mixture.

6. A urea production process as claimed in claim 1, wherein the adiabatic stripping column is operated at a pressure of about 2–5 MPa lower than the reactor-pressure and the mixture formed in step (h) is condensed at a pressure of about 2–5 MPa lower than the reactor pressure.

7. A urea production process as claimed in claim 1, wherein in step (e) said urea solution is contacted with about 90–100% of the carbon dioxide used in said process.

8. A urea production process as claimed in claim 4, wherein the urea solution is concentrated to about 88–95% by weight.

9. A urea production process as claimed in claim 1, wherein in step (e) ammonia is removed until the ratio of $NH_3$ to $CO_2$ unconverted to urea is between about 2.5 and 3.5.

10. A urea production process as claimed in claim 1, wherein the urea solution obtained in step (c) has a ratio of $NH_3$ to $CO_2$ of between about 8 and 10.

11. A urea production process as claimed in claim 2, wherein the third decomposition stage operates at a pressure of about 0.3–0.5 MPa.

12. A urea production process as claimed in claim 3, wherein the amount of fresh ammonia combined with the vapor phase recycle solution mixture is up to about 10% of the total amount of fresh ammonia used in said process.

* * * * *